US00PP21692P2

(12) United States Plant Patent
Lander et al.

(10) Patent No.: US PP21,692 P2
(45) Date of Patent: Feb. 1, 2011

(54) ***PETUNIA* PLANT NAMED 'LAVENDER SKIES'**

(50) Latin Name: *Petunia×hybrida*
Varietal Denomination: Lavender Skies

(75) Inventors: Ken Lander, Pugwash (CA); Mary Maxine Johnson, P.O. Box 403, Pugwash, Nova Scotia (CA) B0K 1L0

(73) Assignee: Mary Maxine Johnson, Pugwash, Nova Scotia (CA)

( * ) Notice: Subject to any disclaimer, the term of this patent is extended or adjusted under 35 U.S.C. 154(b) by 1 day.

(21) Appl. No.: 12/462,109

(22) Filed: Jul. 29, 2009

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP13,542 P2 * 2/2003 Hirabayashi ..... Plt./356
PP13,887 P3 * 6/2003 Bessho ..... Plt./356

OTHER PUBLICATIONS

UPOV ROM GTITM Computer Database, GTI Jouve Retrieval Software 2010/03 Citation for 'Lavender Skies'.*

* cited by examiner

*Primary Examiner*—Wendy C. Haas
(74) *Attorney, Agent, or Firm*—C. A. Whealy

(57) ABSTRACT

A new and distinct cultivar of *Petunia* plant named 'Lavender Skies', characterized by its outwardly spreading, mounding and cascading plant habit; freely branching and vigorous growth habit; early and freely flowering habit; large single flowers that are purple violet in color; flowers that are not persistent; and good garden performance.

1 Drawing Sheet

Botanical designation: *Petunia×hybrida.*
Cultivar denomination: 'LAVENDER SKIES'.

BACKGROUND OF THE INVENTION

The present invention relates to a new and distinct cultivar of *Petunia* plant, botanically known as *Petunia×hybrida* and hereinafter referred to by the name 'Lavender Skies'.

The new *Petunia* plant originated from a cross-pollination in 2005 in Pugwash, Nova Scotia, Canada of two unnamed selections of *Petunia×hybrida,* not patented. The new *Petunia* was discovered and selected by the Inventors as a single flowering plant within the progeny of the stated cross-pollination in a controlled greenhouse environment in Pugwash, Nova Scotia, Canada in October, 2006. Asexual reproduction of the new *Petunia* plant by vegetative cuttings in a controlled greenhouse environment in Pugwash, Nova Scotia, Canada since October, 2006, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Lavender Skies'. These characteristics in combination distinguish 'Lavender Skies' as a new and distinct cultivar of *Petunia:*

1. Outwardly spreading, mounding and cascading plant habit.

2. Freely branching and vigorous growth habit.
3. Early and freely flowering habit.
4. Large single flowers that are purple violet in color.
5. Flowers that are not persistent.
6. Good garden performance.

Plants of the new *Petunia* differ from plants of the parent selections primarily in plant form as plants of the new *Petunia* are more uniform and more cascading than plants of the parent selections.

Plants of the new *Petunia* can be compared to plants of 'Keilavbu', disclosed in U.S. Plant Pat. No. 13,542. In side-by-side comparisons, plants of the new *Petunia* differed from plants of 'Keilavbu' in the following characteristics:

1. Plants of the new *Petunia* were more vigorous than plants of 'Keilavbu'.
2. Plants of the new *Petunia* had smaller and darker green-colored leaves than plants of 'Keilavbu'.
3. Plants of the new *Petunia* were more freely flowering than plants of 'Keilavbu'.
4. Plants of the new *Petunia* and 'Keilavbu' differed in flower color as plants of 'Keilavbu' had sky blue-colored flowers.

Plants of the new *Petunia* can also be compared to plants of 'Kakegawa S28', disclosed in U.S. Plant Pat. No. 13,887. In side-by-side comparisons, plants of the new *Petunia* differed from plants of 'Kakegawa S28' in the following characteristics:

1. Plants of the new *Petunia* were more cascading than plants of 'Kakegawa S28'.
2. Plants of the new *Petunia* flowered later than plants of 'Kakegawa S28'.
3. Plants of the new *Petunia* were more tolerant to low temperatures than plants of 'Kakegawa S28'.

4. Plants of the new *Petunia* and 'Kakegawa S28' differed in flower color as plants of 'Kakegawa S28' had dark purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia*.

The photograph at the bottom of the sheet comprises a side perspective view of a typical plant of 'Lavender Skies' grown in a container.

The photograph at the top of the sheet is a close-up view of typical flowers of 'Lavender Skies'.

DETAILED BOTANICAL DESCRIPTION

The aforementioned photographs and following observations, measurements and values describe plants grown in one-gallon containers in Bonsall, Calif., under commercial practice during the winter and spring in a polyethylene-covered greenhouse with day temperatures ranging from 20° C. to 27° C., night temperatures ranging from 9° C. to 13° C. and light levels ranging from 6,000 to 7,000 foot-candles. Plants were pinched one time and were four months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Lavender Skies'.

Parentage:

*Female, or seed, parent.*—Unnamed selection of *Petunia×hybrida,* not patented.

*Male, or pollen, parent.*—Unnamed selection of *Petunia×hybrida,* not patented.

Propagation:

*Type.*—Terminal vegetative cuttings.

*Time to initiate roots, summer and winter.*—About 10 days at 21° C.

*Time to develop roots, summer and winter.*—About 17 days at 21° C.

*Root description.*—Medium in thickness, fibrous; white, close to 155D, in color.

*Rooting habit.*—Freely branching; moderately dense.

Plant description:

*Form/habit.*—Annual flowering plant; indeterminate; outwardly spreading, mounding and cascading plant habit; vigorous growth habit; freely branching habit with about seven to eight primary lateral branches and numerous secondary and tertiary lateral branches developing per plant; pinching enhances development of lateral branches.

*Plant height.*—About 25 cm.

*Plant diameter* (*area of spread*).—About 62 cm.

*Lateral branches.*—Length: About 37 cm. Diameter: About 4 mm. Internode length: About 1.5 cm to 4 cm. Texture: Pubescent; viscid. Color: Close to 146B to 146C.

Foliage description:

*Arrangement.*—Alternate before flowering; opposite after flowers develop; simple.

*Length.*—About 5.4 cm.

*Width.*—About 2.7 cm.

*Shape.*—Elliptical.

*Apex.*—Acute.

*Base.*—Attenuate.

*Margin.*—Entire.

*Texture, upper and lower surfaces.*—Pubescent; viscid.

*Venation pattern.*—Pinnate, arcuate.

*Color.*—Developing leaves, upper surface: Close to 146B. Developing leaves, lower surface: Close to 146C. Fully expanded leaves, upper surface: Close to 147A; venation, close to 147B. Fully expanded leaves, lower surface: Close to 147B; venation, close to 146D.

*Petioles.*—Length: About 1.2 cm. Diameter: About 4 mm. Texture, upper and lower surfaces: Pubescent; viscid. Color, upper surface: Close to 146C. Color, lower surface: Close to 146D.

Flower description:

*Flower type and habit.*—Single axillary salverform flowers; flowers face upward or outward; freely flowering habit, about 11 to 13 flower buds and open flowers per lateral branch.

*Natural flowering season.*—Long day responsive; long flowering period, early spring until frost in the autumn; flowering continuous during this period; plants begin flowering about six weeks after planting rooted cuttings.

*Flower longevity on the plant.*—About five to six days; flowers not persistent.

*Fragrance.*—Faint; sweet.

*Flower size.*—Diameter: About 5.2 cm. Depth (height): About 5 cm. Tube length: About 3.5 cm. Throat diameter, distal end: About 1.1 cm. Tube diameter, proximal end: About 3 mm.

*Flower buds.*—Length: About 4.5 cm. Diameter: About 8 mm. Shape: Elongated tubular. Color: Close to 92C.

*Petals.*—Quantity/arrangement: About five petals fused in a single whorl, funnelform. Length from throat: About 2.5 cm. Width: About 2.5 cm. Shape: Roughly fan-shaped. Apex: Broadly acute with a central shallow point. Margin: Entire. Texture, petal lobe upper surface: Smooth, glabrous; satiny. Texture, petal lobe lower surface: Sparsely pubescent. Throat texture: Smooth, glabrous. Tube texture: Pubescent. Color: When opening, upper surface: Close to N82B. When opening, lower surface: Close to 91B to 91C. Fully opened, upper surface: Close N81B; venation, close to 188C; color becoming closer to N81C with development. Fully opened, lower surface: Close to N81D; venation, close to 194B. Flower throat (inside): Close to 145C to 145D; venation, close to 145A. Flower tube (outside): Close to 145C; venation, close to 145B.

*Sepals.*—Arrangement/appearance: Single whorl of five sepals fused at base, star-shaped calyx. Length: About 1.9 cm. Width: About 3 mm. Shape: Ligulate. Apex: Rounded. Margin: Entire. Texture, upper and lower surfaces: Pubescent. Color, upper surface: Close to146A. Color, lower surface: Close to146B.

*Peduncles.*—Length: About 2.6 cm. Width: About 1.5 mm. Angle: About 45° from the stem axis. Strength: Strong. Texture: Pubescent; viscid. Color: Close to N144A.

*Reproductive organs.*—Stamens: Quantity per flower: Five. Filament length: About 9 mm. Filament color: Close to 145D. Anther shape: Oval. Anther length:

About 1 mm. Anther color: Close to 155A. Pollen amount: None observed. Pistils: Quantity per flower: One. Pistil length: About 2.2 cm. Style length: About 1.7 cm. Style color: Close to 145D. Stigma shape: Rounded to anvil-shaped. Stigma color: Close to 145A. Ovary color: Close to 145A.

*Seed/fruit.*—Seed and/or fruit production has not been observed.

Pathogen/pest resistance: Plants of the new *Petunia* have not been noted to be resistant to pathogens or pests common to *Petunia*.

Garden performance: Plants of the new *Petunia* have been observed to have good garden performance and have been noted to tolerate temperatures from about 1° C. to about 38° C. and have excellent tolerance to rain and wind.

It is claimed:

1. A new and distinct *Petunia* plant named 'Lavender Skies' as illustrated and described.

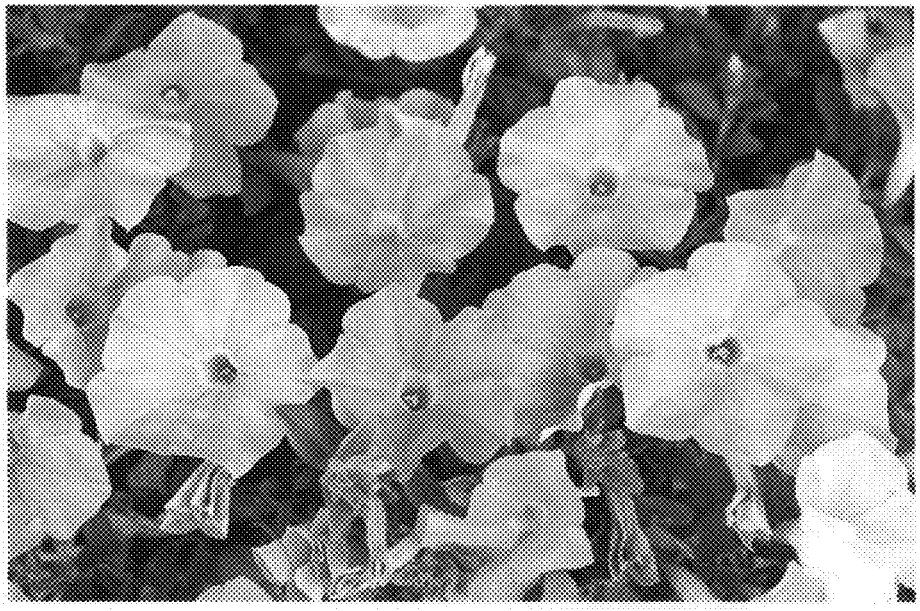
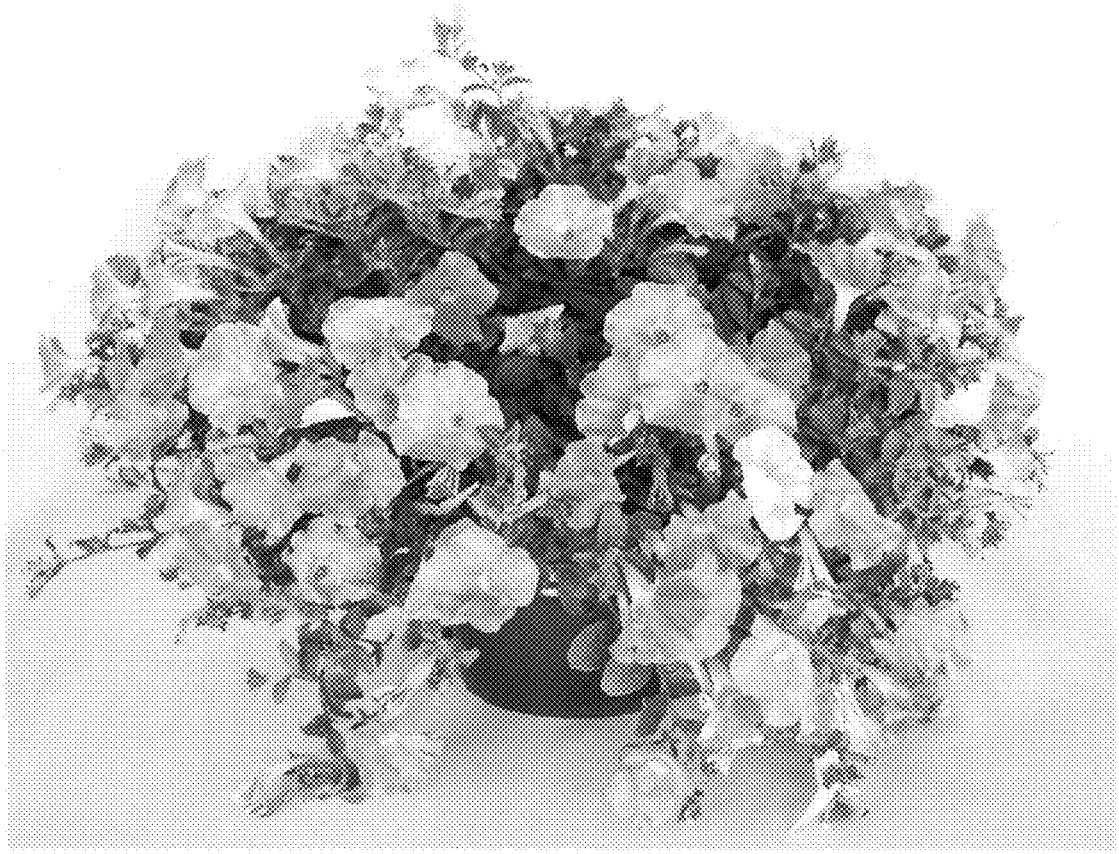

* * * * *